United States Patent [19]

Johns et al.

[11] 4,167,665

[45] Sep. 11, 1979

[54] AUTOMATIC CALIBRATION CIRCUIT FOR GAS ANALYZERS

[75] Inventors: Robert K. Johns, West Covina; Owen M. Houston, Simi Valley; Gene Frick, Los Angeles, all of Calif.

[73] Assignee: Dasibi Environmental Corporation, Glendale, Calif.

[21] Appl. No.: 847,408

[22] Filed: Oct. 31, 1977

[51] Int. Cl.$^2$ .................. G01J 1/32; G01N 21/26; G05D 25/02

[52] U.S. Cl. .................................. 250/205; 250/573

[58] Field of Search .................. 250/205, 573

[56] References Cited

U.S. PATENT DOCUMENTS

| | | | |
|---|---|---|---|
| 3,919,702 | 11/1975 | Hayes et al. | 250/573 X |
| 3,994,601 | 11/1976 | Brugger | 250/573 X |

Primary Examiner—Palmer C. Demeo
Attorney, Agent, or Firm—Lyon & Lyon

[57] ABSTRACT

A device for measuring the concentration of a radiation-absorbing agent in a gas mixture features circuitry for automatically calibrating the device according to a reference gas mixture. An error detector compares the transmittivity of the reference gas mixture, as determined by a photometer, to a reference current determined by Beer's Law. The error signal thus generated is provided to a sample and hold circuit which includes a digital counting circuit and a digital-to-analog converter. The output of the sample and hold circuit causes the drive current supplied to the radiation source of the photometer to be adjusted to automatically calibrate the device.

7 Claims, 3 Drawing Figures

AUTOMATIC CALIBRATION CIRCUIT FOR GAS ANALYZERS

BACKGROUND OF THE INVENTION

This invention relates generally to gas analyzers, and more particularly to automatic calibration circuits utilized in gas analyzers.

Photometric systems have been used with success in measuring concentrations of particular gases, or radiation-absorbing agents, in a gas mixture. For example, such systems have been successfully employed in the measurement of ozone concentrations as shown in U.S. Pat. No. 3,812,330 (assigned to the assignee of the present invention) and the references cited therein, which disclosures are incorporated herein by reference. To determine these gas concentrations, most such devices for determining gas concentrations employ Beer's Law. which states:

$$I = I_o e^{-\alpha LC}$$

where:
I is the intensity of emergent radiation;
$I_o$ is the intensity of incident radiation;
$\alpha$ is the absorptivity of the material at a given frequency;
L is the internal cell length; and
C is the concentration of the gas to be measured.
Alternatively, it may be seen that $$I = I_o \text{ when } C = 0.$$

These variables can be related to the currents which result from the use of a photometer employing a light source and photodetector by the inclusion of a reference offset current, commonly referred to as span current or $I_s$. It can be seen that the variables employed in Beer's Law relate directly to the currents generated in a photometer, or more specifically, $I_o$ is the photometer current when the concentration of the gas to be detected is zero, and I is the measured photometer current for any given sample. Since $I_s$ is a reference offset current, it can be seen that $$I = I_o = -I_s \text{ when } C = 0,$$

$$I + I_s = 0 \text{ when } C = 0.$$

It is also known in the art that $$I_o = SGDA.$$

where S is the intensity of the radiation source;
D is the detector sensitivity;
A is the electrometer gain; and
G is a factor determined from the proportion of light falling on the detector, transmittivity of the optics, background, and other factors.

Difficulties arise because each of these factors may vary with time or temperature. This variation may be described as zero drift. Detection of zero drift is typically made by switching to a reference state in which the gas in the photometer cell does not contain any of the gas to be measured. Correction for zero drift may then be made by adjusting one of these variables until zero drift has been compensated. One device for achieving this is described in the aforementioned U.S. Pat. No. 3,812,330. While the device disclosed in that patent achieved excellent accuracy, the device is complex and expensive. Thus, there has been a need for a simple, inexpensive device for measuring the concentration of a radiation absorbing gas which provides good repeatability and accuracy of measurement.

It is one object of this invention to provide an improved gas analyzer.

It is another object of this invention to provide an improved automatic calibration circuit for use with a gas analyzer.

It is a further object of this invention to provide an automatic calibration circuit to achieve improved span stabilization.

It is another object of this invention to provide an inexpensive automatic calibration circuit for use with a gas analysis device which results in accurate data while enabling long term unattended use.

SUMMARY OF THE INVENTION

As noted previously, ideally the sum of electrometer current (I) and span current ($I_s$) is zero when the concentration of the gas to be detected is zero, or $$I + I_s = 0 \text{ when } C = 0.$$

However, since the electrometer current I depends on $I_o$, if zero drift occurs, $$I + I_s = E \text{ (not zeroed), when } C = 0,$$

where E is an error signal, which those skilled in the art will recognize may be arranged to be either a current or a voltage.

In the present invention, this error signal E is applied to the radiation source through a feedback loop thereby varying the intensity of the source, S. The error signal continues to be applied until the sum of the electrometer current and the span current is returned to zero, thereby calibrating the circuit. After this rezeroing is completed, the intensity of the radiation source is held constant while gas samples containing unknown amounts of the gas of interest are analyzed.

This calibration process is accomplished by interspersing analysis of unknown gas samples with analysis of a reference gas (i.e., a gas having known quantities of the gas to be detected). If the analysis of the reference gas does not yield the expected results, an error signal is sent to a digital sample and hold circuit, which in turn controls the radiation source.

A cycle timer controls both the sample and hold circuit and whether sample or reference gas is placed on the photometer chamber. When sample gas is being analyzed, the sample and hold circuit is placed in the "hold" mode; whereas it is in the "sample" mode when reference gas is analyzed. The bulk of this disclosure is directed to operation when reference gas is being analyzed.

If, upon analysis of the reference gas, zero drift is shown to have occurred, an error detector provides a signal to a sample and hold circuit. The sample and hold circuit includes a digital counter and a digital-to-analog converter (DAC), and controls a drive circuit for the radiation source. The error signal causes the counter to count either up or down, depending upon the polarity of the error, which causes the DAC to adjust the intensity of the radiation source to a level where the electrometer current just matches the references, or span current.

Being thus stabilized, the sample and hold circuit remains at a steady state until the cycle timer runs out, placing the sample and hold circuit in the "hold" mode and causing sample gas to be placed in the photometer chamber. In this manner, considerable accuracy can be obtained in analyzing gas samples, and the foregoing objects of the invention may be achieved.

BRIEF DESCRIPTION OF THE DRAWINGS

The invention, including further objects and advantages thereof, may be better understood by referring to the following detailed description of an embodiment of the invention taken in conjunction with the accompanying drawings in which.

DETAILED DESCRIPTION OF THE INVENTION

Figure 1:
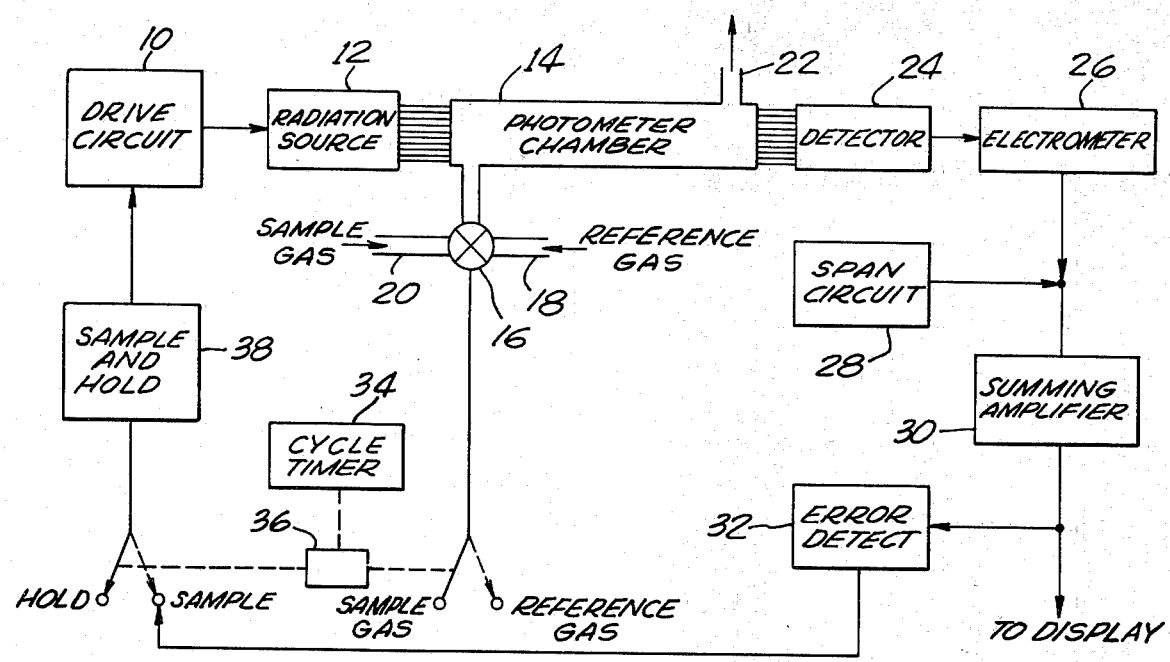
FIG. 1 is a schematic block diagram of a gas analysis system employing the present invention.

Referring now to FIG. 1, a radiation source drive circuit 10 energizes a radiation source 12. For detection of ozone, the radiation source 12 may be a simple ultraviolet light source such as the mercury vapor quartz lamp sold under the tradename Pen Ray Quartz Lamp Model 11 SC-2 by Ultra Violet Products, Inc. For detection of different gases, different wavelengths of radiation may be required; for example, infrared radiations are readily absorbed by gases such as $CO_2$, $H_2S$, $HCN$ and $H_2O$. Hereinafter, the term "radiation" may be used interchangeably with the term "light"; it is to be understood that, in this context, the term "light" is to mean whatever wavelength of radiation is required for detection of the particular gas, and is not limited to the visible spectrum.

The radiation, or light source 12 illuminates a photometer chamber 14, into which either the reference gas or the sample gas may be placed. A gas switch 16 is activated, in a manner described hereinafter, to cause the reference gas to be placed in the photometer chamber 14 through an inlet 18, or the sample gas to be placed in the chamber through an inlet 20. For the detection of ozone, the reference gas will preferably have been "scrubbed" by a filter of manganese dioxide or other suitable filtering material to remove all traces of ozone. A vent 22 is provided in the chamber for the exhausting of the previous gas.

The radiation passing through the photometer chamber from the light source impinges upon a detector 24, which may for example be a photodiode detector sold under the designation R-404 by Hamamatsu TV Company, Ltd. For the detection of ozone, both the light source 12 and the photodetector 24 are configured to operate substantially at 253.7 nanometers; that is, the light source 12 has its output concentrated at that wavelength, and the pass band of the detector is centered at that wavelength. The ends of the sample cell 14 are of course transparent to radiation of this frequency. Thus, the detector senses substantially only the presence of ozone. The detector 24 provides a signal to an electrometer 26, which may be of substantially conventional type.

The output of the electormeter is summed with a precision reference, or span, current from a span circuit 28 in a summing amplifier 30. The output of the summing amplifier 30 provides a system output, which may be displayed in any convenient form, for example, LEDs. The amplifier 30 also provides, when the reference gas is in the photometer chamber 14, a signal to an error detect circuit 32.

A cycle timer 34 controls a solenoid 36, which actuates a gas switch 16 to permit either the sample gas or the reference gas to be placed in the photometer chamber 14. At the same time, cycle timer 34 places a sample and hold circuit 38 in either the sample or the hold state. The sample and hold circuit 38 is, as noted previously, placed in the sample mode when the reference gas is placed in the chamber 14.

Thus, when the timer 34 causes the sample and hold circuit 38 to be placed in the sample mode, the error detector 32 is permitted to supply an error signal to the sample and hold circuit 38. As will be discussed in detail in connection with FIG. 2, when the detector 32 provides an error signal to the sample and hold circuit 38, a signal is supplied to light source drive circuit 10 to adjust the level of the light source 12. The sample and hold circuit continues to adjust, in a manner described in greater detail in connection with FIGS. 2a and 2b, the level of the light source until the signal from the error detector 32 indicates that the sum of the reference current (from the span circuit 28) and the electrometer current is zero. Thereafter, the cycle timer 34 places the sample and hold circuit in the "hold" mode, thereby maintaining the light source at its calibrated level while sample gas is analyzed. In this manner, accurate measurements of ozone concentration may be made when a sample gas is placed in the photometer chamber 14.

Figure 2A:
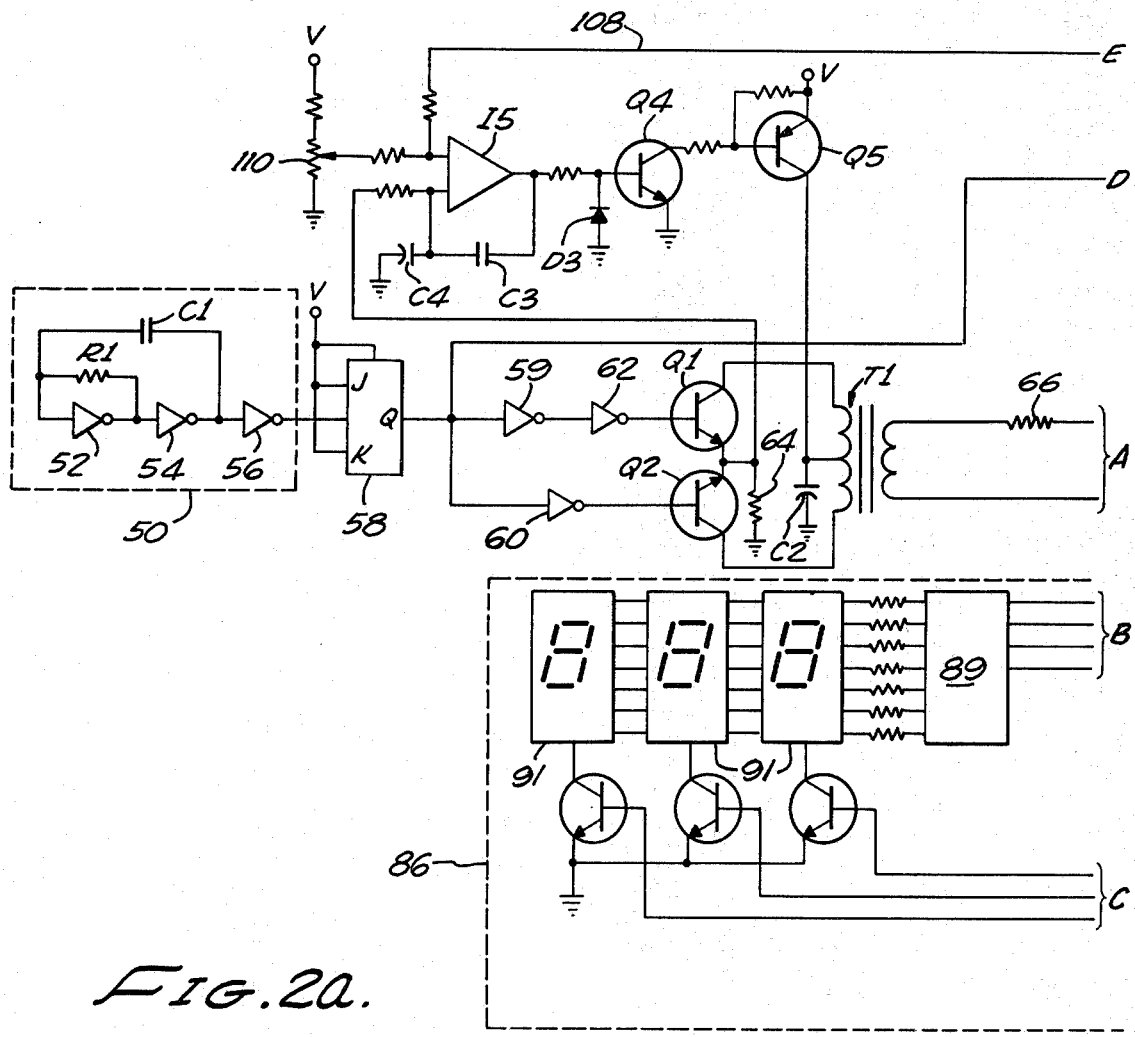
FIGS. 2a-2b are a detailed circuit diagram of the gas analysis system of the present invention.
Figure 2B:
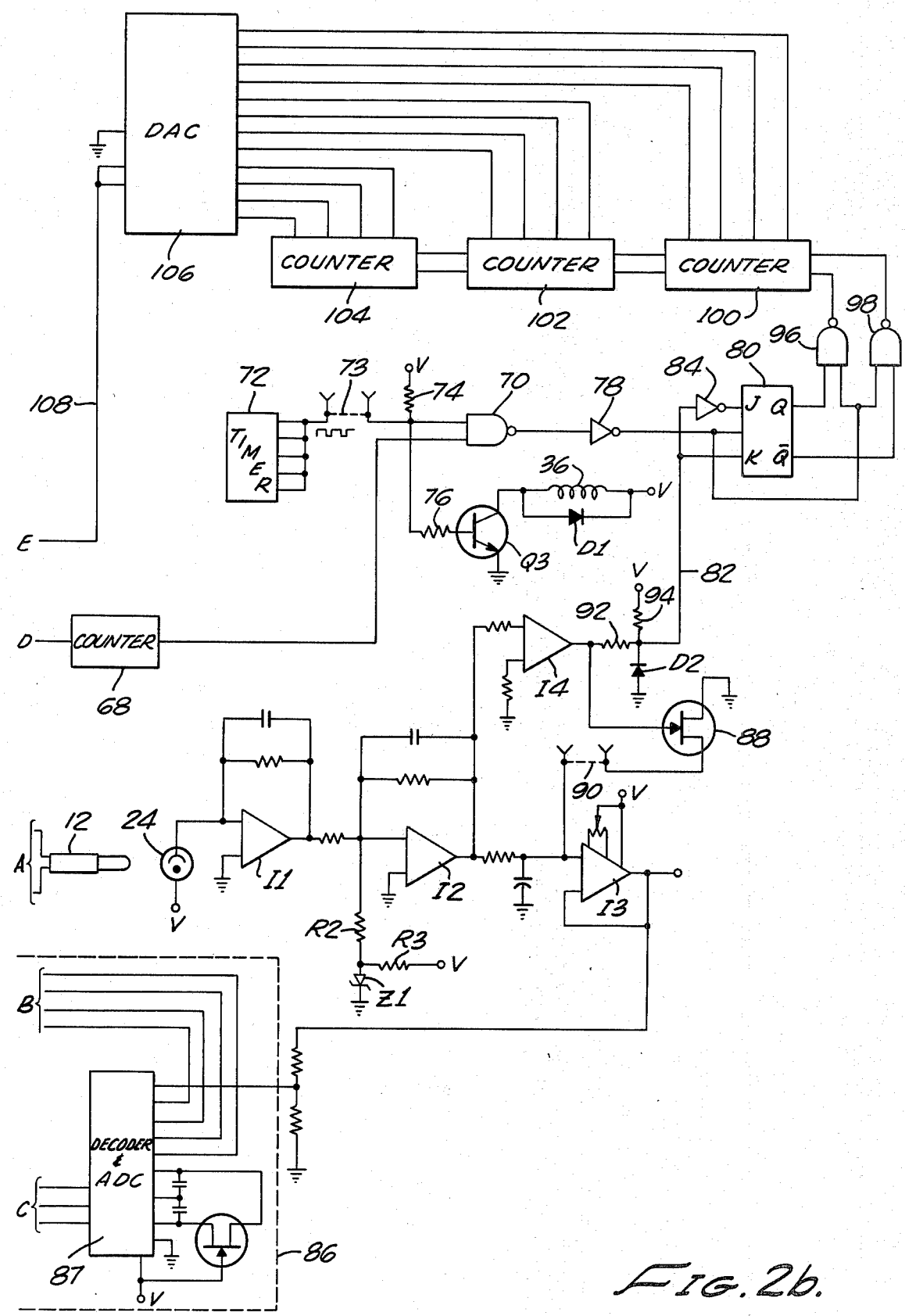

Referring now to FIGS. 2a and 2b, which are joined at the lines designated by letters A-E, respectively, an oscillator 50 is comprised of a trio of inverters 52, 54 and 56, with a resistive feedback path from the input to the output of the inverter 52 and a capacitive feedback path from the output of the inverter 54 to the input of the inverter 52. The output of the oscillator 50 is nominally 20 KHz, although those skilled in the art will recognize that any of a wide range of frequencies is acceptable. The output of the oscillator is provided to a shaping flip-flop 58, for example a JK flip-flop such as the type 74107 arranged in the toggle mode. The flip-flop 58 divides the signal from the oscillator 50 by two, to provide a 10 KHz clock signal. The Q output of the flip-flop 58 provides a signal to a portion of the light source drive circuit, specifically inverters 59 and 60. The inverter 59 provides a signal to another inverter 62, which drives a transistor Q1, typically an NPN transistor. The inverter 60 similarly drives another NPN transistor Q2.

The transistors Q1 and Q2 are coupled to their emitters, which are connected to ground through a resistor 64, such as a 5 Ohm, 10 watt resistor. The collectors of the respective transistors Q1 and Q2 are connected to the primary coil terminals of a transformer T1. The secondary of the transformer T1 drives the light source 12. A resistor 66 may be provided in the secondary circuit of the transformer for current limiting.

The flip-flop 58 also provides the 10 KHz oxcillator output to a decade counter 68, the output of which is nominally a one KHz square wave. This one kilohertz signal is provided as one input to a two input NAND gate 70, the remaining input to which is supplied by a programmable countertimer 72, preferably configured to nominally provide a twenty-second pulse every sixty seconds, or an eighty second cycle. The programmable timer 72 functions as a cycle timer to control the selection of gases to be analyzed and also the operating mode of the sample and hold circuit 38 discussed in FIG. 1. Those skilled in the art will recognize that these cycle times may be varied widely, depending upon the particular application. Thus the timer 72 may be provided with a variable output, both as to pulse-width and duty cycle. A suitable timer is for example the XR 2240 manufactured by Exar Corp., which has a suitably variable output.

The output of the timer 72 is connected to the input of the NAND gate 70 via a jumper 73 for test purposes, to be explained hereinafter. A pull-up resistor 74 may be provided on the output of the timer 72, the remaining terminal of the pull-up resistor 74 being connected to a suitable positive voltage supply "V". Also, the output of the timer 72 is connected to a transistor Q3 through a resistor 76 to drive the solenoid 36.

The emitter of the transistor Q3 is grounded, and the collector of the transistor drives the solenoid coil. The remaining terminal of the solenoid coil is connected to a positive voltage supply, and a diode D1 is connected across the coil of the solenoid for transient protection. It can thus be seen that the solenoid 36 is actuated in response to a pulse from the timer 72, which causes either sample gas or reference gas to be placed in the photometer chamber 14 (FIG. 1), and also causes the sample and hold circuit 38 (FIG. 1) to be placed in either the sample or the hold mode.

The NAND gate 70 provides a signal to an inverter 78, which clocks a second flip-flop 80. Again, the flip-flop 80 may be of the J-K type, with the inverter 78 connected to the clock input thereof. The signal of the J and K inputs is provided from a line 82, with the line 82 being connected directly to the K input and connected to the J input through an inverter 84. The signal on the line 82 is that from the photodetector 24, after substantial amplification. The signal from the photodetector 24 is amplified through a two-stage, low pass amplifier comprised of operational amplifiers I1 and I2, and associated biasing and filtering networks as will be understood by those skilled in the art. Additionally, a buffer-amplifier stage using an operational amplifier I3 is provided to drive a display network, shown generally as 86. The display network 86 includes a decoder-and-ADC 87 such as the type LD130 manufactured by Siliconix, Inc. and also includes a driver circuit 89 such as the type 74C48. A plurality of display devices 91 are also provided in a conventional manner.

The analog output of the amplifiers I1 and I2 is converted to a suitable digital level by means of a comparator I4, connected to the output of the I2 amplifier stage. A FET 88 may be provided between the amplifier stage I2 and a comparator I4 for negative offset protection, with the source of the FET 88 connected, through a jumper 90, to the output of the amplifier stage I2, and the gate of the FET 88 connected to the output of the comparator I4. The drain of the FET 88 is connected to ground. During normal operation, the jumper 90 will be left connected, but may be removed during testing, to cause the circuit to attain predictable reference levels.

The amplifier stage I2 and its associated biasing circuitry perform the functions of the span circuit 28 and the summing amplifier 30, shown in FIG. 1. The precision reference current provided by the span circuit 28 is obtained from a zener diode Z1, such as the type 1N829, and resistors R2 and R3, which are 39.2K and 750, one percent tolerance resistors, respectively. One terminal of each of the resistors R2 and R3 is connected to the anode of the zener diode Z1, the cathode of which is grounded. The remaining terminal of the resistor R3 is connected to a suitable negative voltage supply, for example −15 volts. It should be noted that the voltage supplies described herein are all indicated by a "V", irrespective of the particular voltage and polarity required, since it is believed that one with normal skill in the art can readily ascertain these values.

The amplifier I4 may thus be seen to serve as an error detector, and provides an error signal on line 82, through a resistor 92. A pull-up resistor 94 and a diode D2 are preferably connected to the output of the resistor 92, with the remaining terminal of the resistor 94 being connected to a positive voltage supply and the anode of the diode D2 being connected to ground.

The comparator I4 thus provides a digital level, either high or low, on the line 82. The level on the line 82 is dictated by the zero drift of the system, as detected by the photodetector 24. The level on the line 82, as will become clear shortly, indicates the polarity of the error, and thus determined whether the intensity of the radiation source 12 is to be increased or decreased.

The Q output of the flip-flop 80, which is controlled by the line 82 and the signal into the inverter 78, provides a signal to one input of a two input NAND gate 96. Similarly, the Q-bar input of the flip-flop 80 provides a signal to one input of a two input NAND gate 98. The remaining inputs to each of the two NAND gates 96 and 98 are provided by the output of the inverter 78. The output of the NAND gate 96 provides the down count control signal to a four bit up-down counter 100; the output of the NAND gate 98 provides the up count control signal to the counter 100. Thus it can be seen that the level on the line 82 controls whether the counter 100 and its companion counters 102 and 104 counts up or down. The four bit up-down counter 100, and its companion four bit counters 102 and 104 may be, for example, type 74L193 counters. The counters 100, 102 and 104 are arranged in a conventional ripple carry configuration, and provide twelve outputs to a digital-to-analog converter 106.

The digital-to-analog converter (DAC) 106 may be, for example, a type DAC-80 CBI-V manufactured by Burr-Brown, or other suitable device. The DAC 106 converts the digital signals provided from the counters 100, 102 and 104 to an analog voltage signal applied on line 108 to the remaining portion of the light source drive circuit, comprised of an operational amplifier I5, a reference potentiometer 110, capacitors C3 and C4, and associated biasing circuitry. A feedback path comprised of the capacitor C3 is provided to the negative input of the amplifier I5. The capacitor C4 couples the negative input of the amplifier I5 to ground. The amplifier I5 drives a transistor Q4, typically an NPN transistor, type 2N4238. The transistor Q4 in turn drives a conventionally biased transistor Q5, typically a PNP type 2N4905. The collector of the transistor Q5 is connected to the center terminal of the transformer T1, and also coupled to ground through a capacitor C2.

From the foregoing description, it can be seen that, when the timer 72 allows the reference gas to be placed in the chamber 14, zero drift will be detected by the comparator I4. This in turn will, through the flip-flop 80, cause the counters 100, 102 and 104 to either count up or count down, depending upon the polarity of the zero drift. The pulses counted by the counters, indicating the error, are derived from the oscillator 50. The counter outputs signal the error to the DAC 106, which controls the amplifier stage I5 and therefore the drive circuit for the radiation source 12.

Thus, when the timer 72 enables the flip-flop 80 (i.e., the "sample" mode) the intensity of the radiation source 12 is adjusted until the sum of the reference signal and the electrometer current is zero. The output of the comparator I4 then stabilizes at a level where the counters 100, 102 and 104 cycle around a zero count by counting up one increment down one increment. The circuit remains in this stabilized condition until the timer 72 disables the flip-flop 80, thereby placing the sample and hold circuit 38 (FIG. 1) in the "hold" mode. Sample gas, which is now permitted to enter the chamber 14 (FIG. 1), may now be analyzed accurately, since zero drift has automatically been compensated. With this arrangement, analysis of gas samples with repeatabilities of ±20 parts per billion has been achieved.

While an exemplary embodiment of the invention has been described, it is to be understood that the invention is not limited to the details herein explained. It is expected that those skilled in the art will recognize numerous variations and equivalents which come within the spirit of the invention and are intended to be included herein.

We claim:

1. An automatic calibration circuit for use with apparatus for measuring the concentration of a radiation-absorbing agent in a gas mixture, comprising
   a radiation source arranged to irradiate a detector, amplifier means adapted for receipt of a signal from said detector,
   error detecting means responsive to said amplifier means for providing an error signal, and
   sample and hold means responsive to said error signal for varying the level of radiation emitted from said radiation source unit said error detecting means indicates a predetermined level, said sample and hold means including a digital-to-analog converter.

2. The automatic calibration circuit of claim 1 wherein said sample and hold means includes a digital counter.

3. The automatic calibration circuit of claim 1 further including
   reference signal means in communication with said amplifier means for determining a reference level for said error detecting means.

4. An automatic calibration circuit for use with apparatus for measuring the concentration of a radiation-absorbing agent in a gas mixture comprising
   amplifier means adapted to receive a signal from a detector,
   error detecting means responsive to said amplifier means for providing an error signal,
   counter means responsive to said error signal, and
   digital-to-analog converter means responsive to said counter means and adapted to drive a source of radiation configured to irradiate a detector, said digital-to-analog converter means being configured to vary the intensity of radiation from said source until said error detecting means indicates substantially no error signal.

5. The automatic calibration circuit of claim 4, wherein said counter means is bidirectional.

6. The automatic calibration circuit of claim 5 further including
   level conversion means responsive to said error detecting means for causing said counter means to count up when said level conversion means is in a first state, and to count down when said level conversion means is in a second state.

7. An automatic calibration circuit for use with gas analysis apparatus comprising
   reference signal means for generating a reference signal,
   summing amplifier means having an output and adapted to receive signals from a detector and to sum said signals with said reference signal,
   error signal means responsive to said summing amplifier means,
   bidirectional counter means responsive to said error signal means for counting in a first direction if said error signal is in a first state, and counting in a second direction if said error signal is in a second state,
   digital-to-analog converter means responsive to said counter means and adapted for connection to a radiation source for varying the level of radiation emitted by said source until said error signal means indicates substantially no error.

* * * * *